United States Patent [19]

Ogawa et al.

[11] Patent Number: 4,601,977

[45] Date of Patent: Jul. 22, 1986

[54] METHOD FOR MEASURING THE ACTIVITY OF PLASMA FACTOR XIII

[75] Inventors: Kazuo Ogawa; Setsuko Baba, both of Chiba; Kazuo Nakanishi, Yokohama, all of Japan

[73] Assignee: Iatron Laboratories, Inc., Tokyo, Japan

[21] Appl. No.: 502,473

[22] Filed: Jun. 9, 1983

[30] Foreign Application Priority Data

Jun. 11, 1982 [JP] Japan ................................. 57-99284

[51] Int. Cl.$^4$ ............................................. C12Q 1/56
[52] U.S. Cl. ..................................................... 435/13
[58] Field of Search .................... 435/13; 436/537, 56, 436/172

[56] References Cited

U.S. PATENT DOCUMENTS 4,161,515 7/1979 Ullman ............................... 436/537
4,235,869 11/1980 Schwarzberg ...................... 436/537
4,245,040 1/1981 Pilgeram ............................... 435/13

OTHER PUBLICATIONS

Takahashi et al.–Chem. Abst. vol. 91 (1979), p. 153874s.
Lorand et al.–J. Clin. Invest. vol. 48 (1969), pp. 1054–1064.

Primary Examiner—Sam Rosen
Attorney, Agent, or Firm—Albert L. Jeffers; Stephen T. Belsheim

[57] ABSTRACT

In determining blood coagulation factor XIII in plasma, the activity of XIIIa, an activated form of the factor XIII, is measured by a method using casein and a fluorescent cadaverine derivative as the substrate and also featuring use of molecular sieve chromatography for separating a cadaverine derivative reacted with casein and an unreacted compound.

2 Claims, 3 Drawing Figures

METHOD FOR MEASURING THE ACTIVITY OF PLASMA FACTOR XIII

BACKGROUND OF THE INVENTION

This invention relates to the measurement of blood coagulation factor XIII in plasma. More particularly, the invention relates to a process for measuring the plasma factor XIII by determining the activity of XIIIa, an activated form of the factor XIII, by a fluorescence method in which reacted fluorescent material and non-reacted fluorescent material are separated by means of molecular sieve chromatography to accurately measure the amount of the reacted fluorescent material.

Plasma factor XIII is an enzyme which is effective in the final stage of blood coagulation. More precisely, it is categorized as a non-active enzyme which shows its enzymatic activity only when it is converted into form XIIIa by the action of thrombin and $Ca^{++}$ in plasma. It is therefore possible to determine the amount of plasma factor XIII by measuring the activity of XIIIa.

The action of XIIIa in the blood coagulation mechanism consists in forming intermolecular crosslinkage, in other words, isopeptide bonds between fibrins produced by the action of thrombin, and thus XIIIa is deemed to have a transglutaminase activity. Because of these peculiarities, this plasma factor has a very great clinical significance, and its importance is acknowledged especially in the detection of disseminated intravascular coagulation (DIC) and kidney diseases and in the clinical examination in the fields of surgery and obstetrics. Incidentally, a report by the DIC research group of the Ministry of Public Welfare backs up such utility of plasma factor XIII. The development of a simple and accurate method of measuring this plasma factor XIII, therefore, has been strongly desired.

Various methods such as mentioned below have been deviced for the measurement of plasma factor XIII:

(1) Clot test method: The solubility of fibrin gel in urea or an acid is examined. This method is simple but rather lacks accuracy of determination.

(2) Crosslink determination method: Crosslinked lysine in fibrin gel is determined. This method requires a large volume of specimen and is also unsatisfactory in quantitative accuracy.

(3) Radioisotope method: The amount of a $^{14}C$ compound incorporated into casein is measured. This method is excellent in determination accuracy and high in sensitivity but has drawbacks mentioned below.

(4) Fluorescence method: Incorporation of dansylcadaverine into casein is determined. This method is high in both measurement accuracy and sensitivity but rather complicated in operation.

(5) Antigen-antibody method: This method is of a medium degree in both sensitivity and accuracy of determination but has a problem that the antigen activity and the enzyme activity are not always consistent with each other because of a wide difference in antigenecity between the factor XIII and its activated form XIIIa.

Thus, a variety of methods have been proposed for measurement of the factor XIII, among which the radioisotope (RI) method and fluorescence method are believed to be excellent in both sensitivity and accuracy of determination. However, the RI method necessitates a substantial investment for the equipment as a radioactive substance is treated. This method is also complicated in operation and unsuited for a small-scale practice. The fluorescence method is free of such problems of the RI method but still has some serious disadvantages as discussed below. This method was first reported by Lorand et al in 1969 (J. Clin. Invest., 48: 1054–1064, 1969). According to this method, a casein-dansylcadaverine complex is formed by bonding γ-glutamyl groups of casein and ε-amino groups of dansylcadaverine by the action of XIIIa as depicted by the following formula:

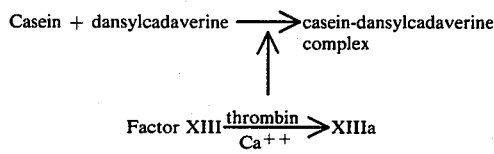

This casein-dansylcadaverine complex is precipitated by using a strong acid and repeatedly washed with an organic solvent. After separating unreacted dansylcadaverine by washing, the precipitate is dissolved in an aqueous solution of urea containing a surfactant and the fluorescence intensity of the solution is measured. From the measured value of fluorescence intensity, both the activity of XIIIa and the quantity of the factor XIII are determined.

This method, although excellent in many points, is yet unsatisfactory in some respects. It is an essential requirement in this method to separate the casein-dansylcadaverine complex free of unreacted dansylcadaverine, which necessitates use of a strong acid and an organic solvent. Use of such matters, however, is undesirable in a practical test. Also, washing of the precipitate with an organic solvent is troublesome, and much time and labor is often required for the perfect separation of entrapped unreacted dansylcadaverine. Because of these defects, this method could hardly be applied to the routine clinical tests.

SUMMARY OF THE INVENTION

The present inventors have made extensive studies for overcoming these defects of Lorand's method and, as a result, found that by taking advantage of the far greater molecular weight of casein-dansylcadaverine complex than that of free dansylcadaverine, these two compounds can be separated from each other very easily and perfectly by using molecular sieve chromatography. This invention was achieved on the basis of this finding.

Thus, this invention provides a method for determining blood coagulation factor XIII in plasma by measuring the activity of its activated form XIIIa by using casein and a fluorescent cadaverine derivative as the substrate, characterized by use of polyvinyl alcohol for separating a cadaverine derivative reacted with casein and an unreacted compound.

DETAILED DESCRIPTION OF THE INVENTION

The casein used in this invention is a mixed protein having a molecular weight of about 75,000 to 375,000 while dansylcadaverine is a compound having a naphthalene ring with a molecular weight of 355.5. The caseindansylcadaverine complex, therefore, may be regarded to have almost the same molecular weight as casein. Such a great difference in molecular weight between the two substances helps to enhance the effect of molecular sieves especially.

The cadaverine derivative used in this invention is not limited to any specific types but may be suitably selected from those which are fluorescent per se and can retain the fluorescence even when they are bonded to casein. Such cadaverine derivatives include, for example, coumarin derivatives such as fluorescein and anthracene and naphthalene derivatives such as dansylcadaverine. Among them, dansylcadaverine is particularly most preferred.

Figure 1:
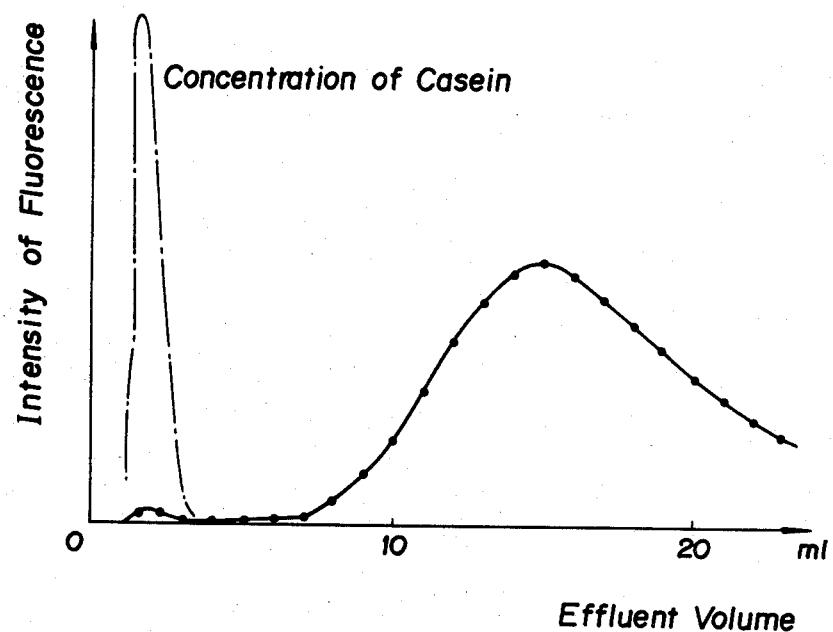
FIG. 1 shows a graphic elution pattern when a mixed solution of casein and dansylcadaverine was developed with a buffer solution in a column.

As the column gel for molecular sieving in this invention, one can use, polyvinyl alcohol. Because of the large difference in molecular weight between the substances to be separated in this invention, a conventional column gel used for desalting can well serve for the purpose of this invention. When such a gel is used, the casein-dansylcadaverine complex is eluted together with casein after the void volume. Elution of unreacted dansylcadaverine occurs far later. This relation is graphically illustrated in FIG. 1. One may use dextran, agarose, polyacrylamide, spherical cellulose as the column gel also, but polyvinyl alcohol is preferable especially. The testing method comprises adding 1 ml of a mixed solution of casein and dansylcadaverine as specimen into a column such as one used in the Example described later and developing it with a buffer such as one used in the Example. As apparent from the results shown in FIG. 1, 95% of casein is eluted during the period of initial 3 ml elution, but dansylcadaverine is scarcely eluted during this stage; its substantial elution begins well after this initial 3 ml elution. Therefore, the fluorescence of dansylcadaverine that can be measured at the time of initial elution of casein is one which originates in the casein-dansylcadaverine complex, so that by measuring the intensity of this fluorescence it is possible to determine the activity of XIIIa and accordingly the amount of plasma factor XIII. Although other high-molecular weight substances such as protein are eluted within this stage, the measurement of fluorescence is not the least affected by such matter.

EXAMPLE

1. Reagents (1) Buffer solution: 0.05 mol/l tris-HCl solution (pH 7.5)
(2) Thrombin solution: Thrombin was dissolved in the above buffer solution containing 0.05% of bovine serum albumin to prepare a 100 U/ml solution.
(3) Casein solution: Casein was dissolved in the above buffer solution to prepare a 1.0% solution of casein.
(4) Dansylcadaverine solution: Dansylcadaverine was dissolved in the above buffer solution to prepare a 2.0 mmol/l solution.
(5) Calcium chloride solution: Calcium chloride was dissolved in the above buffer solution to prepare a 130 mmol/l solution.
(6) Reaction stopper: 12 mmol/l maleimide solution.

2. Operation

20 $\mu$l of plasma was sampled and added to 0.1 ml of the buffer solution (1) containing 10% glycerol and the mixture was heated at 56° C. for 4 minutes and then cooled with ice. To this solution were added 0.2 ml of the dansylcadaverine solution, 0.1 ml of the casein solution, 0.05 ml of the calcium chloride solution and 0.05 ml of the thrombin solution in that order and the mixture was reacted at 37° C. for 10 minutes. Immediately thereafter, 0.1 ml of the reaction stopper (6) was added to stop the reaction. 0.5 ml of the resulting solution was poured into the top of the column. When the whole solution has penetrated, 2.5 ml of the buffer solution (1) was added. When the effluent from the bottom of the column has become 3 ml, the fluorescence intensity of this 3 ml effluent was measured in the known way and the activity of XIIIa and the amount of the factor XIII were calculated from the measured value of the fluorescence intensity. The excitation wavelength was 335 nm and the measurement wavelength was 510 nm. The column used in this test was of a cylindrical type of 1.6 cm in diameter. 1 ml of polyvinyl alcohol particles ("Toyopearl HW-40, Coarse", a product of Toyo Soda Co., Ltd.) was used as gel.

Figure 2:
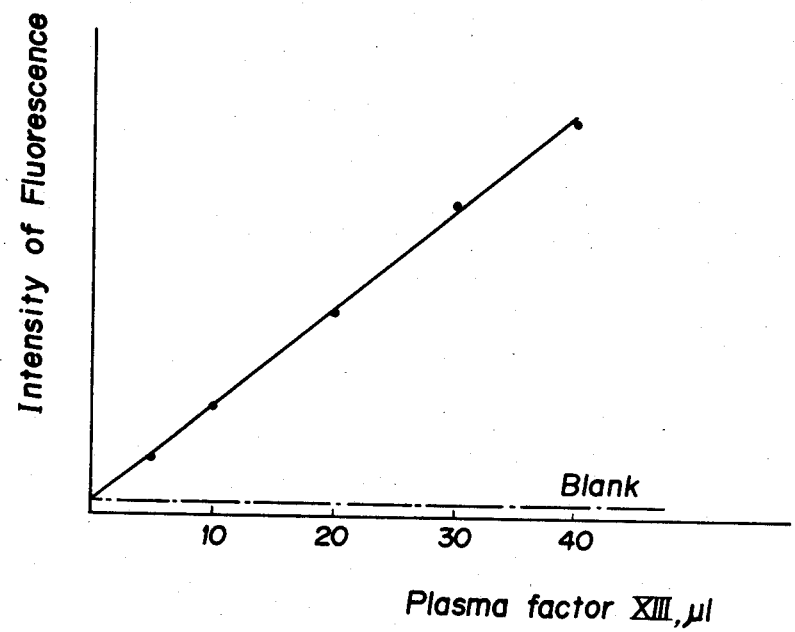
FIG. 2 is a graph showing the relationship between the quantity of plasma factor XIII and the intensity of fluorescence.
Figure 3:
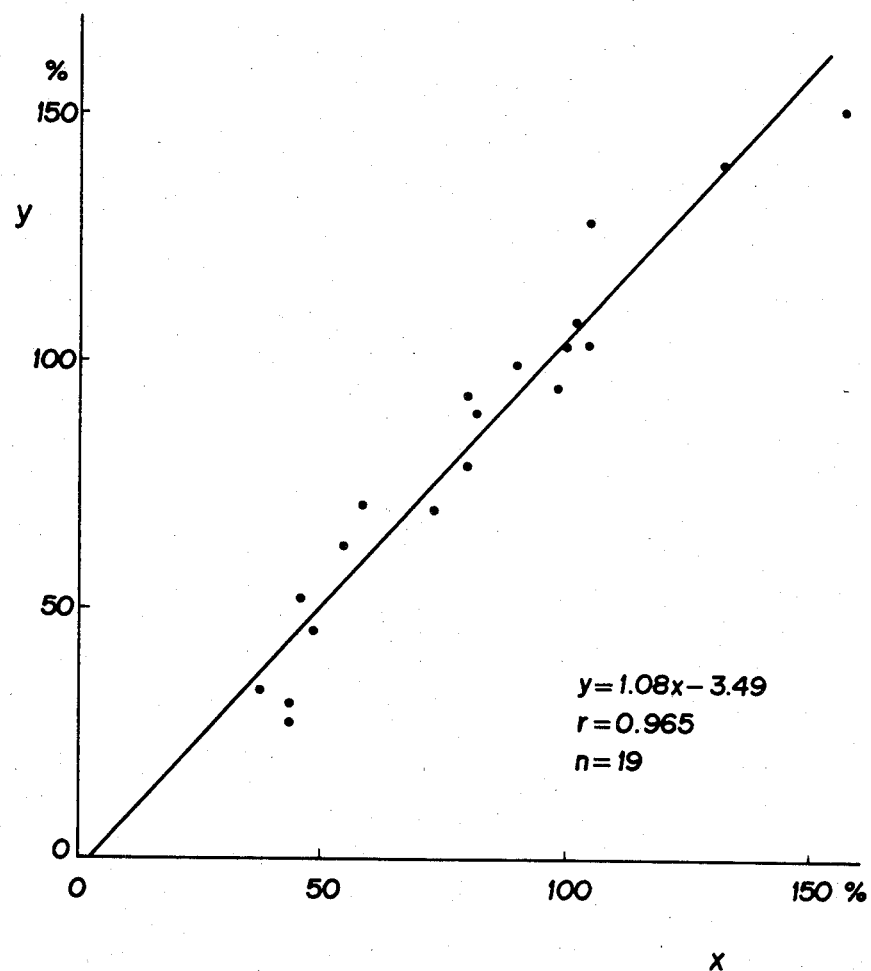
FIG. 3 is a graph showing the interrelation between the method of this invention (represented on the ordinate) and Lorand's method (represented on the abscissa).

The results of the tests conducted on various amounts of specimen in the manner described above are shown in the graph of FIG. 2. The graph evidently showed adaptability of this method to the quantitative determination. The reproducibility of the respective specimens as determined by measuring the relative ratio of fluorescence intensity was 100, 104, 105, 99, 105, 105, 101, 103 and 98, the coefficient of variation (CV) being only 2.6%, with the average reproducibility of the normal persons being given as 100.

Thus, the method of this invention using a high-sensitivity reaction system is simple in operation and capable of providing accurate values of determination. It is thus a very useful method which can be conveniently applied to the routine clinical tests and examinations.

What is claimed is:

1. A method for determining blood coagulation factor XIII in plasma by measuring the activity of its activated form XIIIa by using casein and a fluorescent cadaverine derivative as the substrate, characterized by use of polyvinyl alcohol as a column gel for molecular sieves for separating a cadaverine derivative reacted with casein and a cadaverine derivative not reacted with case.

2. The method according to claim 1 wherein the cadaverine derivative is dansylcadaverine.

* * * * *